United States Patent
Miles et al.

(10) Patent No.: US 10,092,296 B2
(45) Date of Patent: *Oct. 9, 2018

(54) APPLICATOR FOR SURGICAL CLIPS

(71) Applicant: Femcare-Nikomed Limited, Hampshire (GB)

(72) Inventors: Desmond John Miles, Basingstoke (GB); John Philip Briant, Letchworth (GB); Adrian John Streeter, Peterborough (GB); James Daniel John, Cambridge (GB); Iain Grierson McDerment, Hertfordshire (GB); Nick Harrison, Cambridge (GB); Robin Eddington, Cambridge (GB)

(73) Assignee: FEMCARE-NIKOMED LIMITED, Romsey, Hampshire (GB)

( * ) Notice: Subject to any disclaimer, the term of this patent is extended or adjusted under 35 U.S.C. 154(b) by 533 days.

This patent is subject to a terminal disclaimer.

(21) Appl. No.: 14/682,670

(22) Filed: Apr. 9, 2015

(65) Prior Publication Data

US 2015/0265282 A1    Sep. 24, 2015

Related U.S. Application Data

(62) Division of application No. 13/121,731, filed as application No. PCT/GB2009/002347 on Oct. 2, 2009, now Pat. No. 9,451,966.

(30) Foreign Application Priority Data

Oct. 3, 2008  (GB) .................................. 0818101.8

(51) Int. Cl.
*A61B 17/10* (2006.01)
*A61B 17/128* (2006.01)
(Continued)

(52) U.S. Cl.
CPC .... *A61B 17/1285* (2013.01); *A61B 17/00234* (2013.01); *A61B 17/068* (2013.01);
(Continued)

(58) Field of Classification Search
CPC ........ A61B 17/1285; A61B 2090/0811; A61B 2090/0814; A61B 17/00234;
(Continued)

(56) References Cited

U.S. PATENT DOCUMENTS 3,775,825 A   12/1973  Wood et al.
3,954,108 A   5/1976   Hugh
(Continued)

FOREIGN PATENT DOCUMENTS

CA   2 559 770   3/2007
DE   90 15 046   1/1991
(Continued)

*Primary Examiner* — Jing Ou
(74) *Attorney, Agent, or Firm* — Renner, Otto, Boisselle & Sklar, LLP

(57) ABSTRACT

A hand-operable surgical clip applicator (10) including a barrel (12) having a first end (14) and a second end (16), the second end formed to accommodate a surgical clip, a crimping lever (20) pivotally connected at the second end of the barrel, and a trigger (28) co-located with the barrel, the trigger being operable to pivot the crimping lever, the pivoting movement of the crimping lever causing the surgical clip to be urged from an open position to a closed position, wherein the trigger has an operating portion on either side of the barrel.

8 Claims, 6 Drawing Sheets

(51) Int. Cl.
 *A61B 17/04* (2006.01)
 *A61B 17/068* (2006.01)
 *A61B 17/00* (2006.01)
 *A61B 17/29* (2006.01)
 *A61B 90/00* (2016.01)

(52) U.S. Cl.
 CPC ............ *A61B 17/10* (2013.01); *A61B 17/128* (2013.01); *A61B 2017/00424* (2013.01); *A61B 2017/00438* (2013.01); *A61B 2017/00584* (2013.01); *A61B 2017/00725* (2013.01); *A61B 2017/0488* (2013.01); *A61B 2017/2919* (2013.01); *A61B 2017/2925* (2013.01); *A61B 2017/2936* (2013.01); *A61B 2090/0811* (2016.02); *A61B 2090/0814* (2016.02)

(58) Field of Classification Search
 CPC ..... A61B 17/068; A61B 17/10; A61B 17/128; A61B 2017/00424; A61B 2017/00438; A61B 2017/00584; A61B 2017/00725; A61B 2017/0488; A61B 2017/2919; A61B 2017/2925; A61B 2017/2936
 See application file for complete search history.

(56) References Cited

U.S. PATENT DOCUMENTS

| | | | | |
|---|---|---|---|---|
| 4,369,788 A * | 1/1983 | Goald | ............... | A61B 17/1608 600/564 |
| 4,712,549 A | 12/1987 | Peters et al. | | |
| 5,100,420 A | 3/1992 | Green et al. | | |
| 5,156,608 A | 10/1992 | Troidl et al. | | |
| 5,464,144 A * | 11/1995 | Guy | ................... | A61B 17/072 128/104.1 |
| 5,542,949 A | 8/1996 | Yoon | | |
| 5,720,756 A | 2/1998 | Green et al. | | |
| 5,810,877 A * | 9/1998 | Roth | ................ | A61B 17/1285 606/174 |
| 5,817,128 A | 10/1998 | Storz | | |
| 5,826,776 A | 10/1998 | Schulze et al. | | |
| 6,162,207 A | 12/2000 | Ouchi | | |
| 6,241,740 B1 | 6/2001 | Davis et al. | | |
| 7,552,854 B2 | 6/2009 | Wixey et al. | | |
| 2002/0165549 A1 | 11/2002 | Owusu-Akyaw et al. | | |
| 2002/0198537 A1 * | 12/2002 | Smith | .................. | A61B 17/122 606/139 |
| 2004/0044352 A1 * | 3/2004 | Fowler | ................ | A61B 17/128 606/142 |
| 2004/0097970 A1 * | 5/2004 | Hughett | ............ | A61B 17/1285 606/142 |
| 2005/0070925 A1 | 3/2005 | Shelton, IV et al. | | |
| 2005/0139636 A1 * | 6/2005 | Schwemberger | .... | A61B 17/072 227/180.1 |
| 2006/0079913 A1 | 4/2006 | Whitfield et al. | | |
| 2007/0084897 A1 * | 4/2007 | Shelton, IV | ...... | A61B 17/07207 227/176.1 |
| 2007/0179499 A1 | 8/2007 | Garrison | | |
| 2008/0109016 A1 * | 5/2008 | Bright | .................... | A61B 17/10 606/142 |
| 2008/0140090 A1 * | 6/2008 | Aranyi | ............... | A61B 17/1285 606/143 |
| 2008/0188872 A1 | 8/2008 | Duff | | |
| 2009/0302091 A1 * | 12/2009 | Shah | ................ | A61B 17/07207 227/180.1 |
| 2009/0302093 A1 * | 12/2009 | Kasvikis | .............. | A61B 17/072 227/180.1 |
| 2009/0308909 A1 * | 12/2009 | Nalagatla | ......... | A61B 17/07207 227/180.1 |

FOREIGN PATENT DOCUMENTS

| | | |
|---|---|---|
| EP | 0 622 049 | 11/1994 |
| EP | 0 732 078 | 9/1996 |
| EP | 0 885 595 | 12/1998 |
| EP | 1 175 869 | 1/2002 |
| EP | 1 609 427 | 12/2005 |
| EP | 1 757 239 | 2/2007 |
| EP | 1 974 676 | 10/2008 |
| WO | 95/34246 | 12/1995 |
| WO | 99/52413 | 10/1999 |
| WO | 02 080783 | 10/2002 |
| WO | 2008/127968 | 10/2008 |

\* cited by examiner

APPLICATOR FOR SURGICAL CLIPS

CROSS-REFERENCES TO RELATED APPLICATIONS

This is a divisional of U.S. patent application Ser. No. 13/121,731, filed Jul. 25, 2011, now U.S. pat. No. 9,451,966; which is a national phase application under 35 U.S.C. § 371 of International Patent Apppplication No. PCT/GB2009/002347, filed Oct. 2, 2009, and published in the English language.

TECHNICAL FIELD

This application relates to applicators for surgical clips, and more particularly to applicators for the insertion and closure of surgical clips.

BACKGROUND OF THE INVENTION

Such applicators are intended for single handed operation by an operating surgeon. Examples of such applicators are described in international patent application publication numbers WO 2005/039422 and WO-A-01/12079.

Such clips may be used for sterilisation or other medical, orthopaedic or surgical purposes. An example is the "Filshie" clip which is disclosed in GB patent number 2177748.

Certain known applicators for such clips, as disclosed for example in WO 2005/039422, use a pushrod and associated linkage mechanism to cause rotation of an articulated jaw to produce compression forces on a clip and to thereby compress the clip causing it to close, preferably with a latching action. The compression forces on the relatively slender pushrod cause radial reaction forces and consequent friction at the interface between the pushrod and the outer tube. This can result in the applicator mechanism sticking in the closed position thus causing problems for the operating surgeon in disengaging the applicator from the closed clip.

Another problem with known applicators is the need to adjust the travel of the mechanism in order to achieve correct closure of the clip to an accurate position; such adjustment can be costly to achieve. It is important that the surgical clip is closed to an accurate position. If the clip is closed too tightly, the tubular anatomy may be severed, requiring the surgeon to apply further clips to severed ends of the tubular anatomy. Conversely, if applied clips are not closed sufficiently tightly, the tubular anatomy may not be properly occluded.

A further problem with known applicators is the requirement that the applicator must be made from expensive components in order to ensure that the surgical clips can be closed accurately, and to be able to perform many clip closure operations. In particular, in such an important piece of medical equipment, and especially one in which mechanical forces are transmitted (e.g. the force of the surgeon pulling the trigger, which is converted to a closing force on the clip), it is important that tolerances are carefully monitored and, if need be, adjusted in the manufacturing environment. This can be expensive, and increases the manufacturing cost of the applicator.

Appropriate design of applicator and its constituent components can mitigate some of the issues associated with this.

Other designs of applicators can require the surgeon to apply significant force to the trigger mechanism of the applicator in order to correctly close and latch the surgical clip, which can make the applicator difficult to manipulate and operate.

It is often necessary for the applicator to be inserted into a cannula during "keyhole" surgery. Existing clip applicators have a "pistol" handgrip which can make them difficult to manipulate into the correct position whilst at the same time operating the applicator (in particular providing adequate manual closure force) to close the clip.

It is an object of the invention to provide an applicator for surgical clips which requires less force to operate and to correctly close and secure a surgical clip than known applicators.

Another object of the invention is to provide an applicator which can precisely close and secure surgical clips to an accurate position.

A further object of the invention is to provide an applicator which may be more precisely manipulated than known applicators, whilst also being operable to close and secure accurately a surgical clip.

A still further object of the invention is to provide an applicator for surgical clips which is of a simpler and more robust design to such known applicators.

Yet another object of the invention is to provide an applicator for surgical clips which is easier and cheaper to manufacture than existing applicators Such an applicator may be partially or completely disposable.

SUMMARY OF THE INVENTION

According to a first aspect of the invention there is provided a hand-operable surgical clip applicator, the applicator comprising a barrel having a first end and a second end, the second end formed as a first crimping surface and being able to accommodate a surgical clip; a crimping lever, the crimping lever pivotally connected to the barrel, the crimping lever having a second crimping surface and a opening peg, the second crimping surface being in opposition to the first crimping surface, the first crimping surface and the second crimping surfaces being biased away from one another; and a pushrod, slidably located within the barrel, which may abut, and in use does abut, the crimping lever and constrains the opening peg; wherein movement of the pushrod towards the second end of the barrel causes the pushrod to push the crimping lever, further causing the second crimping surface to close onto the first crimping surface, thereby in use urging a surgical clip from an open position towards a closed position.

In known applicators it is common for the second end of the pushrod to slide over the crimping lever in order to rotate the crimping lever about a hinge point and urge the surgical clip from an open position to a closed position. This can result in the crimping lever becoming jammed in the closed position due to the frictional forces between the second end of the pushrod and the crimping lever.

In the present invention, linear movement of the pushrod towards the second end of the barrel results in the second end of the pushrod pushing against the crimping lever. This causes a rotational movement of the crimping lever. During opening of the crimping surfaces, the second end of the pushrod acts to pull on the opening peg of the crimping lever to thereby cause the crimping lever to move such that the crimping surfaces are in an open position.

Preferably, movement of the pushrod away from the second end of the barrel causes the pushrod to pull the opening peg, further causing the second crimping surface to open away from the first crimping surface.

Preferably the pushrod includes a hollow portion, with a return spring being accommodated within the hollow portion.

Locating the return spring within the pushrod ensures that the surgical clip will be released from the applicator in the event that any part of the handle, trigger or actuating means should fail in use, thereby improving reliability of the applicator.

Preferably the barrel is formed from a single piece of material.

This can be achieved by utilising a forming process which facilitates the manufacture of the first crimping surface and the pivot on which the crimping lever is mounted from the same piece of tubing material. This avoids welding of barrel components, which has previously been necessary where the barrel and parts of the barrel have been made by machining.

Forming the barrel from a single piece of material reduces the number of component parts in the applicator, making it easier to assemble and lowering the manufacturing cost.

According to a further aspect of the invention there is provided a hand-operable surgical clip applicator, the applicator comprising a barrel, the barrel having a first end and a second end, the second end formed to accommodate a surgical clip; a crimping lever; a trigger; and a handle; wherein the handle includes a first lever having a first end and a second end, the first end of the first lever being pivotally connected at the handle, the second end of the first lever being slidably connected to the trigger; and a second lever having a first end, a second end and a centre region, the centre region of the second lever being pivotally connected to the handle, the first end of the second lever being configured to slide along the length of the first lever, the second end of the second lever being adapted to operate the crimping lever; the first lever and the second lever being configured to provide a mechanical advantage between the trigger and the crimping lever, movement of the trigger in use causing movement of the crimping lever, resulting in a surgical clip being urged from an open position to a closed position.

The use of a mechanism to provide a mechanical advantage such as that described above between the trigger and the crimping lever enables the manual actuation force required to be provided by the user to be reduced, thereby making the applicator easer to operate.

The concomitant increase in trigger travel allows the surgeon to more precisely determine the degree of trigger movement required to correctly close and secure the surgical clip.

A compound lever arrangement as described above is a simple and effective means of providing a mechanical advantage.

Preferably the barrel includes a slot at its first end, the slot accommodating the second end of the second lever.

The slot in the first end of the barrel allows the pushrod to be located completely within the barrel.

Preferably the first end of the pushrod includes an end cap, the second end of the second lever pressing against the end cap.

The end cap located at the first end of the pushrod provides an increased surface area against which the second end of the second lever presses. This eliminates the possibility that the second end of the second lever will become disengaged from the first end of the pushrod during operation of the applicator.

Preferably the pushrod further comprises a transfer rod and a pusher, the pusher having a stop face, the transfer rod and pusher being slidably located within the barrel, the transfer rod and pusher being releasably connected together by a bayonet joint and the pusher abutting the crimping lever and constraining the opening peg of the crimping lever.

By connecting the pushrod and the pusher with a bayonet joint, the pusher experiences no bending forces which may cause it to bind in the barrel.

Preferably, the pusher is formed with sliding surfaces at each of the first and second ends, the sliding surfaces configured to slide within the internal surface of the barrel, the portion of the pusher between the first and second ends having a smaller diameter than each of the first and second ends.

Such a pusher has a waisted profile which facilitates insertion of the pusher into the barrel during assembly of the applicator. The waisted feature also reduces the friction between the pusher and the barrel during operation of the applicator.

Preferably the trigger includes a visual indicator in at least one side thereof, the visual indicator providing means indicative of an intermediate trigger position.

If the clip is incompletely closed, the clip may partially latch which will prevent the clip from subsequently being correctly latched. The visual indicator in the trigger allows the surgeon to partially close the clip so that it can be inserted through a cannula, without the risk of the clip becoming partially latched, prior to the clip being applied to a tubular anatomy.

Preferably the barrel is located in the handle by a barrel pin, the barrel pin being secured to the handle.

The barrel pin secures the barrel directly to the handle. This feature ensures that the forces generated during the clip closure process are transmitted to the handle.

Preferably the handle includes a locating plate, the locating plate being secured to the barrel by a retaining pin, the locating plate being further secured to the handle by a locating plate fastener.

The function of the locating plate is to position the barrel securely relative to the handle. This enables the surgeon to manipulate the applicator precisely.

An additional function of the locating plate is to provide a secondary positive stop to the trigger. This secondary stop provides the surgeon with clear, tactile feedback that the mechanism has reached the end of its travel. Once the mechanism has reached the end of its travel, the secondary stop transmits the loads applied to the trigger directly to the handle. This prevents the mechanism from being damaged due to the application of excessive force to the trigger.

Preferably the pushrod includes a slot, the slot accommodating the retaining pin.

The retaining pin serves to secure the barrel to the locating plate.

Preferably the stroke of the pushrod is limited by the stop face of the pusher abutting the crimping lever.

By governing the stroke of the pushrod, the stop face of the pusher abutting the crimping lever provides a first end stop to the travel of the trigger and the consequent rotation of the crimping lever. This prevents the crimping lever from closing the surgical clip past the nominal closed position. Such "over-closing" can result in the clip being closed too tightly.

According to a further aspect of the invention there is provided a hand-operable surgical clip applicator, the applicator comprising a barrel, the barrel having a first end and a second end, the second end formed to accommodate a surgical clip; a crimping lever; and a trigger, the trigger co-located with the barrel, the trigger being adapted to operate the crimping lever, causing the surgical clip to be urged from an open position to a closed position, wherein the trigger is formed with a pressing surface disposed on each of two opposing sides of the barrel.

In use, the clip applicator must be manipulated into the correct position and simultaneously operated to apply the surgical clip to a tubular anatomy, such as a Fallopian tube. By arranging the trigger on either side of the barrel, the clip applicator can be more precisely positioned, whilst manually applying force to close the clip. This is because the barrel is positioned between the first and second fingers of the surgeon's hand, making it align naturally to the wrist of the surgeon, thus assisting the surgeon in precisely positioning the barrel. Such a trigger configuration may also be ergonomically more suitable, allowing the muscles of the surgeon's hand to more readily generate a closing force than a conventional trigger configuration.

A further advantage of this embodiment may be that as the trigger is moved into and out of the handle there is no appreciable gap between the trigger and the body of the handle. In surgical operation surgical gloves will be worn which may be snagged and torn if there were to be any substantial gap between the trigger and the handle, which could cause hygiene issues.

Preferably, at least one of the trigger, handle, first lever, second lever or locating plate is formed from a material which becomes molten when the applicator is exposed to the operating environment within a medical autoclave.

Conveniently, the applicator is a disposable device which is intended for use on a single patient. A desirable safety feature of the applicator is that at least one of the main operating components of the applicator is formed from a material which melts when exposed to the conditions operating environment within a medical autoclave. Thus, the applicator can be rendered unusable if the unit was to be sterilised in an autoclave.

DESCRIPTION OF THE DRAWINGS

There now follows a description of preferred embodiments of the invention, by way of non-limiting example, with reference being made to the accompanying drawings, in which.

DETAILED DESCRIPTION

Figure 1:
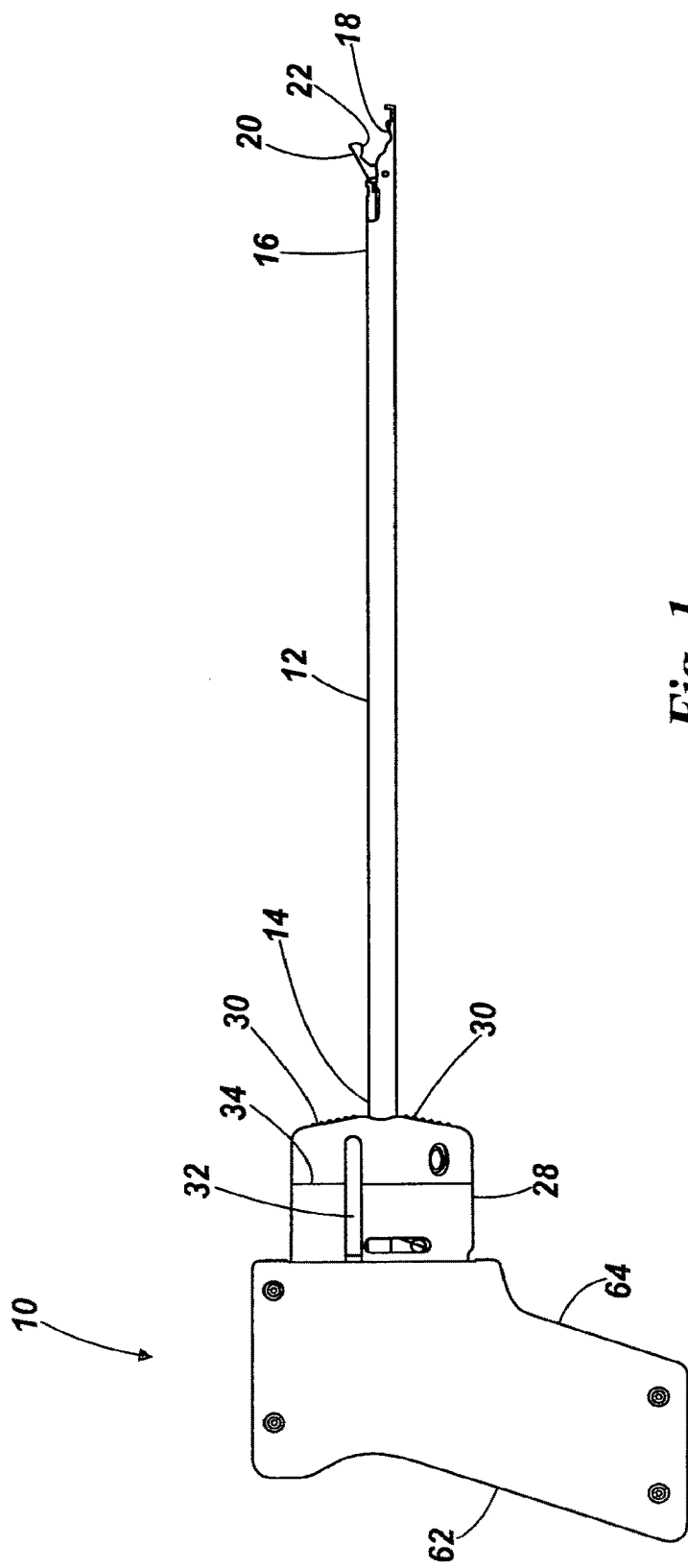
FIG. 1 shows a perspective view of the applicator of the invention.

With reference to the drawings, FIG. 1 shows a hand-operable surgical clip applicator according to the invention.

The applicator 10 comprises a barrel 12, a trigger 28 and a handle 62.

The barrel 12 has a first end 14 and a second end 16. The second end of the barrel 16 is formed as a first crimping surface 18 and accommodates a surgical clip.

The barrel 12 is formed from a single piece of stainless steel tubing.

Figure 2:
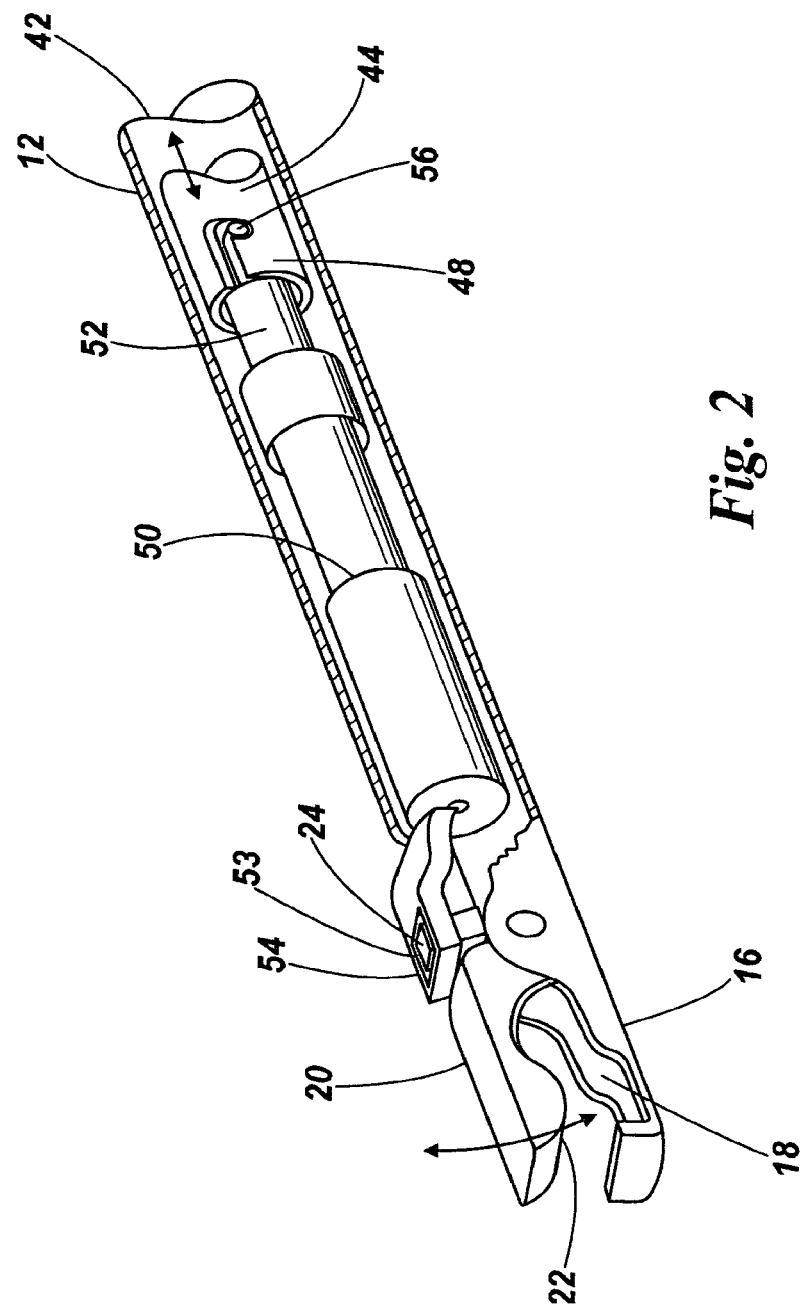
FIG. 2 shows a partial sectional perspective view of the second end of the barrel of the applicator of FIG. 1.
Figure 3:
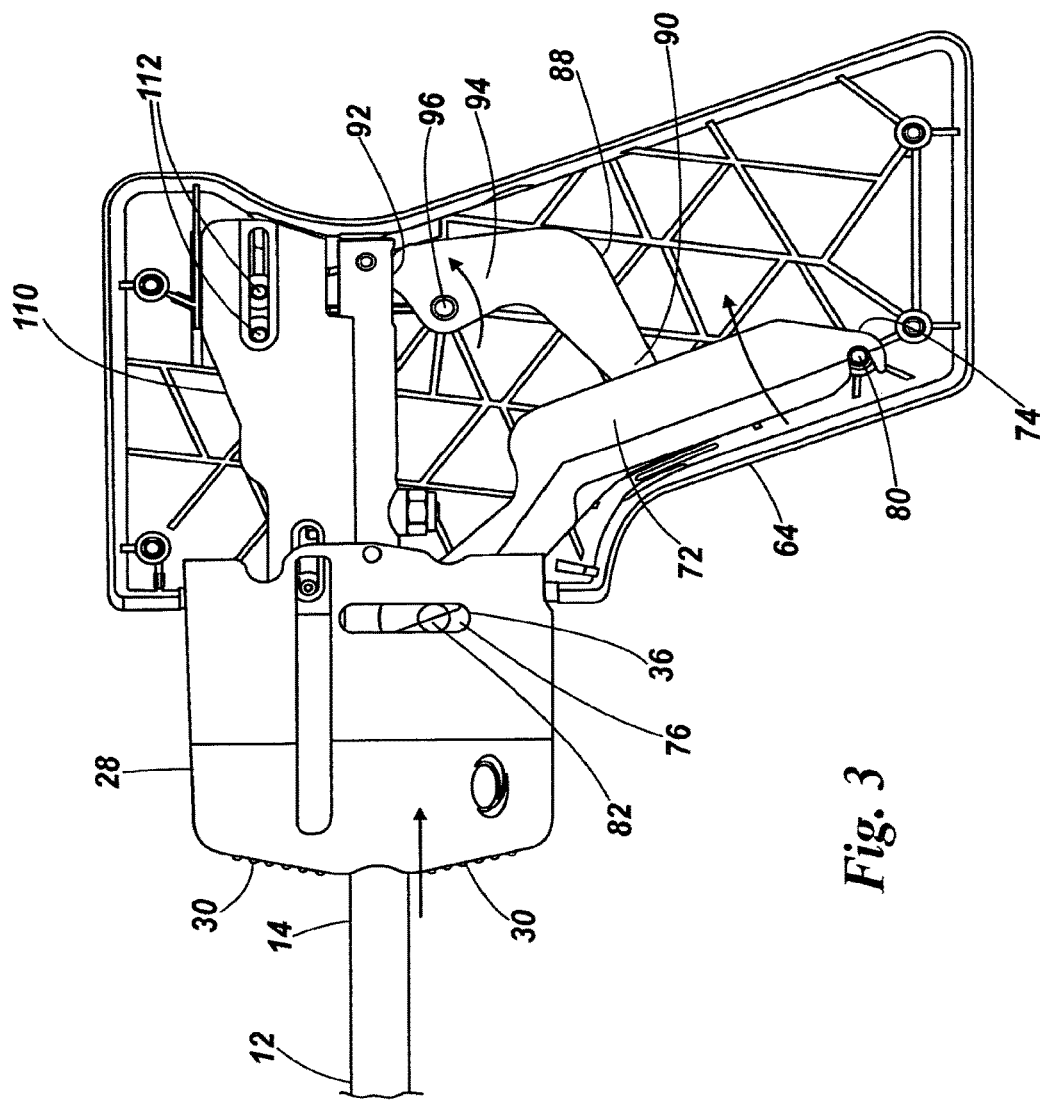
FIG. 3 shows a sectional view of the handle of the applicator of FIG. 1.

As shown in FIG. 2, a crimping lever 20 is pivotally mounted at the second end of the barrel 16. The crimping lever 20 has a second crimping surface 22 and an opening peg 24 formed integrally.

The second crimping surface 22 of the crimping lever 20 and the first crimping surface 18 at the second end of the barrel 16 act as a co-operative pair of jaws to crimp the surgical clip and to urge the clip from an open position to a closed position.

As shown in the figures, a pushrod assembly 42 is slidably located within the barrel 12 and comprises a transfer rod 44 and a pusher 50.

The transfer rod 44 has a first end 46 and a second end 48. The pusher 50 has a first end 52 and a second end 54.

Figure 4:
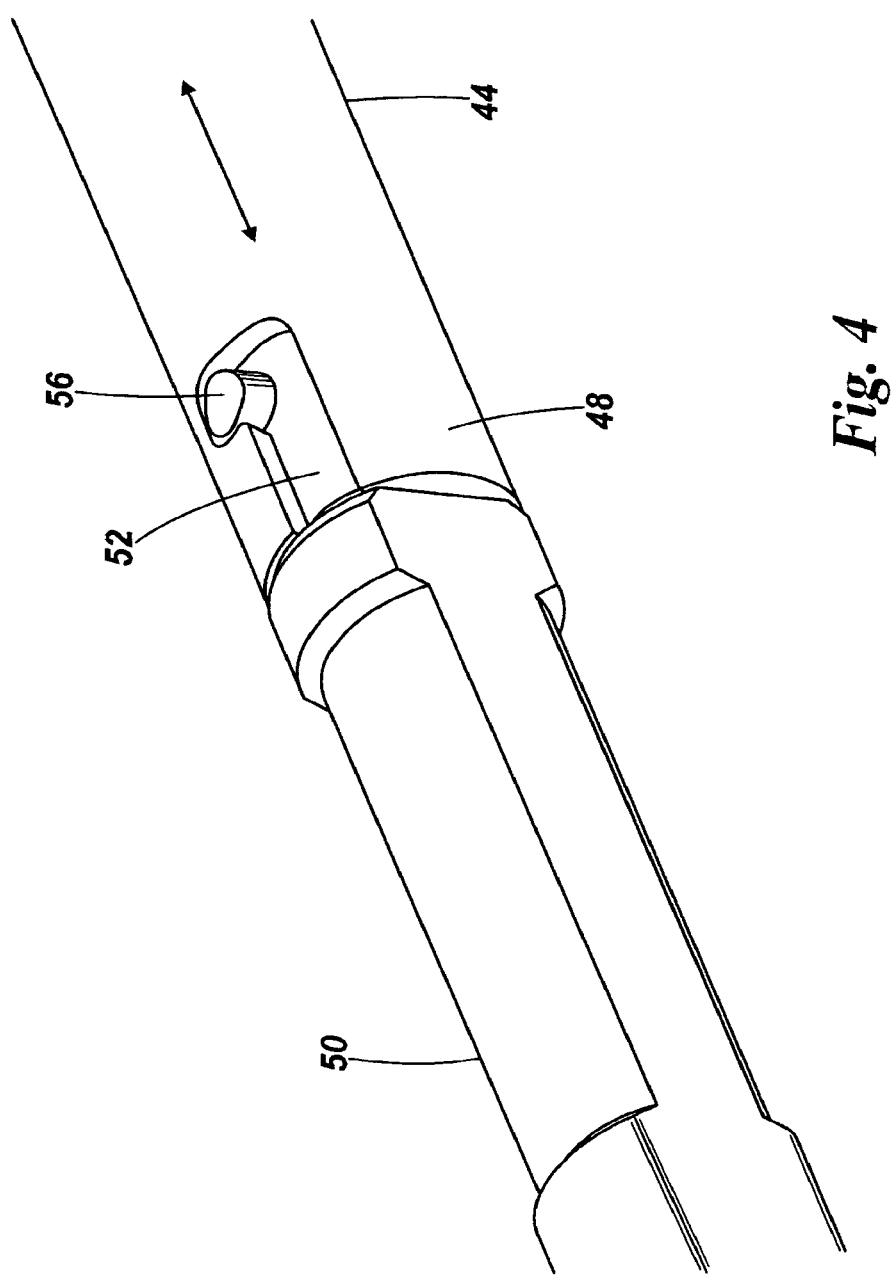
FIG. 4 shows a partial sectional view of the bayonet joint of the applicator of FIG. 1.

The second end 54 of the pusher 50 is formed with a slot 53 which constrains the opening peg 24 of the crimping lever 20 and a stop face 55. The first end 52 of the pusher 50 is operatively coupled to the second end 48 of the transfer rod 44 by a bayonet coupling 56, as shown in FIG. 4.

The pusher 50 is waisted and is formed with sliding surfaces at each of the first and second ends 52,54 which slide along the internal surface of the barrel 12. This waisted feature facilitates assembly of the pusher 50 into the barrel; the waisted feature also reduces the friction between the pusher 50 and the barrel 12, compared to if the whole of the pusher 50 had a consistent radius along its length.

The trigger 28 is co-located with the barrel 12 and includes a pressing surface 30 on each of two opposing sides of the barrel 12. Each of the pressing surfaces 30 is sized to be operable by the first and second fingers of the surgeon's hand respectively.

The trigger is preferably moulded from a thermoplastic material.

The trigger 28 includes a visual indicator 32 in each side of the trigger 28. The visual indicator 32 takes the form of a slot in each side of the trigger 28 with a reference mark 34 moulded into the side surface of the trigger 28.

The visual indicator 32 provides a visual indication of an intermediate or "half closed" trigger position. When the trigger 28 is depressed such that the reference mark 34 is aligned with a locating plate 110, the trigger 28 is "half closed". This can be important as it allows the surgeon to operate the applicator 10 to hold and partially close the surgical clip without latching the clip, thus enabling the applicator and the clip to be inserted through the cannula prior to being positioned, closed and secured.

The trigger 28 further includes an actuating slot 36 on each side of the trigger which is part of a lever mechanism.

The handle 62 is formed in two parts. The handle 62 is preferably moulded from a thermoplastic material.

The handle 62 includes a first lever 72 and a second lever 88. The first lever 72 has a first end 74 and a second end 76. The second lever 88 has a first end 90, a second end 92 and a centre region 94.

The first end 74 of the first lever 72 is pivotally connected to the handle 62 by a first pivot 80. The second end 76 of the first lever 72 is slidably connected to the trigger 28. Two actuating pegs 82 formed on opposing sides of the second end 76 of the first lever 72 engage with the actuating slot 36 of the trigger 28.

The first lever 72 is formed with a U-shaped cross-section. The first lever 72 is preferably moulded from a thermoplastic material.

The centre region 94 of the second lever 88 is pivotally connected to the handle 62 by a second pivot pin 96. The first end 90 of the second lever 88 is arranged to slide along the length of the first lever 72 with the first end 90 of the second lever 88 located within the U-shaped profile of the first lever 72. The second end 92 of the second lever 88 presses against the first end of the transfer rod 46.

The second lever 88 is preferably formed from stainless steel.

The first lever 72 and the second lever 88 are configured to provide a mechanical advantage between the trigger 28 and the transfer rod 46.

Figure 5:
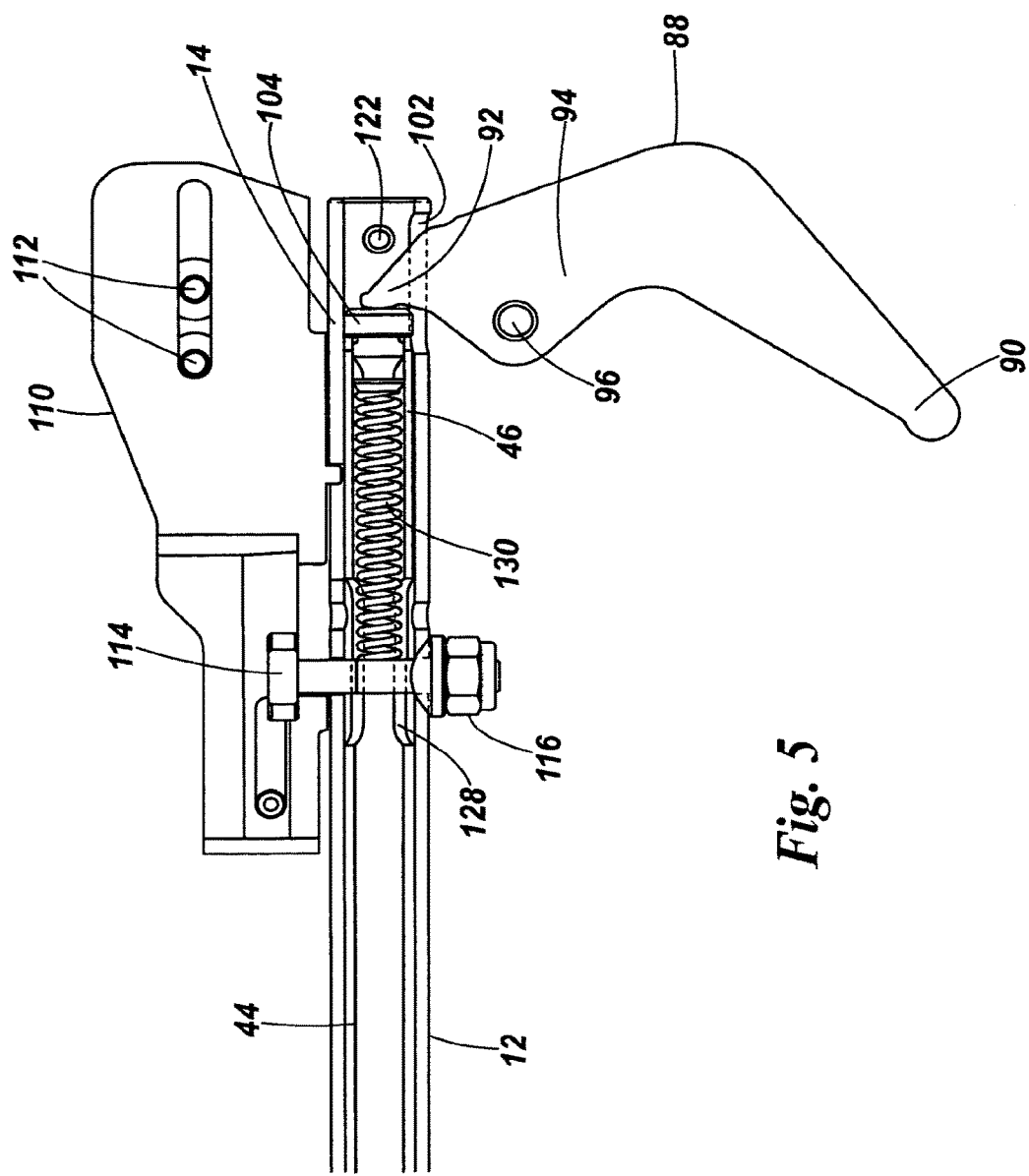
FIG. 5 shows a detailed partial sectional view of the first end of the barrel of the applicator of FIG. 1.
Figure 6:
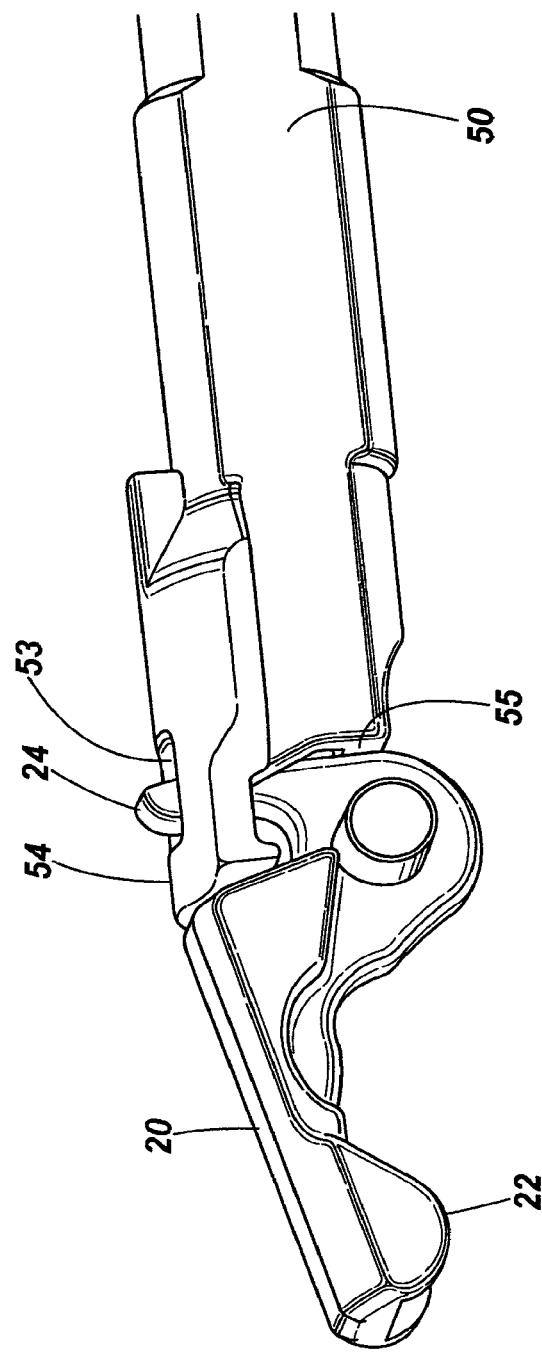
FIG. 6 shows the operation of the first end stop of the applicator of FIG. 1.

FIG. 5 shows a detail view of the first end 14 of barrel 12.

The barrel pin 122 secures the first end 14 of the barrel 12 to the handle 62.

The locating plate 110 is secured to the first end 14 of the barrel 12 by the retaining pin 114. The retaining pin 114 may be a nut and bolt or an alternative type of fastener.

The retaining pin 114 passes through a hole in the first end 14 of the barrel 12 and through a slot 128 in the transfer rod 44.

The slot 128 in the transfer rod 44 allows for the linear movement of the transfer rod 44.

The locating plate 110 is secured to the handle by two locating plate screws 112. The locating plate screws 112 pass through a slot in the locating plate 110. The slot in the locating plate allows movement of the locating plate 110 relative to the handle 62 for calibration purposes. This calibration is described in more detail below.

An end cap 104 is located in the first end 46 of the transfer rod 44. The second end 92 of the second lever 88 presses against the end cap 104.

A return spring 130 is located within the first end 46 of the transfer rod 44 between the end cap 104 and the retaining pin 114.

Calibration

The closure of the surgical clips to the correct position is set by a first end stop formed by the stop face 55 of the pusher 50 abutting the crimping lever 20. The position of this first end stop is not adjustable, being governed by the dimensions of the pusher 50 and the crimping lever 20.

The locating plate 110 provides a second end stop feature by limiting movement of the trigger 28. The position of this second end stop must be adjusted to match the first end stop position, during the assembly of the applicator.

The second end stop feature provides the surgeon with clear, tactile feedback that the trigger has been depressed sufficiently to fully close and secure the surgical clip.

An additional benefit of the second end stop is that it limits the force which the surgeon can apply via the trigger to the compound lever mechanism, which might otherwise damage the handle or other parts of the applicator.

The adjustment of the position of the second end stop is made by moving the locating plate 110 within the handle 62 until the second end stop position matches the first end stop position. The locating plate 110 is then secured to the handle 62 with the locating plate screws 112.

Operation

The applicator 10 is intended to be used single-handedly. The trigger 28 is intended to be operated by the first and second fingers with the handle 62 accommodating the remaining fingers.

When the trigger 28 is depressed it slides into the handle 62. There is minimal clearance between the trigger 28 and the handle 62. When the applicator is being used, the surgeon will be wearing surgical gloves. Any substantial gap between the trigger 28 and the handle 62 may result in the surgical glove becoming trapped and torn, which could create hygiene problems.

Movement of the trigger 28 results in the actuating pegs 82 on the second end 76 of the first lever 72 being moved by the actuating slot 36 in the trigger 28.

As the first lever 72 rotates around the first pivot pin 80, the first end 90 of the second lever 88 slides along the length of the actuating surface 78 of the first lever 72, thereby rotating the second lever 88 about the second pivot pin 96.

Rotational movement of the second lever 88 causes the second end 92 of the second lever 88 to press against the end cap 104 of the transfer rod 44 causing linear movement of the transfer rod 44.

Linear movement of the transfer rod 44 and pusher 50 towards the second end 16 of the barrel 12 causes the second end 54 of the pusher 50 to push against the crimping lever 20 causing rotational movement about the pivot point of the crimping lever 20. This movement of the crimping lever 20 results in the second crimping surface 22 of the crimping lever 20 closing onto the first crimping surface 18 at the second end 16 of the barrel 12 resulting in the surgical clip being urged from an open position to a closed position.

When the second crimping surface 22 reaches a position relative to the first crimping surface 18 in which the surgical clip is closed to the correct position, a first end stop limits further movement of the crimping level 20. The first end stop is formed by the stop face 55 of the pusher 50 abutting the crimping lever 20. The first end stop ensures that the surgical clip is precisely closed to the correct position and is not "over-closed".

Additional pressure applied to the trigger after the first end stop has been actuated results in a second end stop coming into operation. The second end stop is formed by the trigger directly contacting the locating plate, thus further limiting the stroke of the mechanism.

When the trigger 28 is released, the return spring 130 urges the transfer rod 44 and pusher 50 away from the second end 16 of the barrel 12. Linear movement of the transfer rod 44 and pusher 50 away from the second end 16 of the barrel 12 causes the slot 53 at the second end 54 of the pusher 50 to pull against the opening peg 24 of the crimping lever 20 causing rotational movement about the pivot point of the crimping lever 20. This movement of the crimping lever 20 results in the second crimping surface 22 of the crimping lever 20 opening away from the first crimping surface 18 at the second end 16 of the barrel 12.

What is claimed is:

1. A hand-operable surgical clip applicator, the applicator comprising:
   a barrel having a first end and a second end, the second end formed as a first crimping surface and being able to accommodate a surgical clip;
   a crimping lever, the crimping lever pivotally connected to the barrel, the crimping lever having a second crimping surface and an opening peg integrally formed therewith, the second crimping surface being in opposition to the first crimping surface, the first crimping surface and the second crimping surface being biased away from one another; and
   a pushrod, slidably located within the barrel, to selectively abut the crimping lever;
   wherein movement of the pushrod towards the second end of the barrel causes the pushrod to push the crimping lever, further causing the second crimping surface to close onto the first crimping surface, thereby in use urging a surgical clip from an open position towards a closed position;

wherein the pushrod includes a slot through which a portion of the opening peg extends, the pushrod thereby constraining movement of the opening peg;

wherein the pushrod further includes a transfer rod and a pusher, the pusher having a stop face, the transfer rod and the pusher being slidably located within the barrel, the transfer rod and pusher being releasably connected together by a bayonet joint, the pusher abutting the crimping lever, and the pusher having the slot that constrains movement of the opening peg; and wherein movement of the pushrod away from the second end of the barrel causes the pushrod to pull the opening peg, further causing the second crimping surface to open away from the first crimping surface.

2. An applicator as claimed in claim 1 in which the pushrod includes a hollow portion, with a return spring being accommodated within the hollow portion.

3. An applicator as claimed in claim 1 in which the barrel is formed from a single piece of material.

4. An applicator as claimed in claim 1 further including a handle which includes a first lever having a first end and a second end, and a second lever having a first end, and a second end; and wherein a first end of the pushrod includes an end cap, and the second end of the second lever presses against the end cap.

5. An applicator as claimed in claim 1, the pusher being formed with sliding surfaces at each of a respective first and a respective second end of the pusher, the sliding surfaces configured to slide within the internal surface of the barrel, a portion of the pusher between the first and second ends of the pusher having a smaller diameter than each of the first and second ends of the pusher.

6. An applicator as claimed in claim 1 including a locating plate, the locating plate being secured to the barrel adjacent the first end by a retaining pin, and wherein the slot in the pushrod constraining the opening peg is a first slot, and the pushrod includes a second slot that accommodates passage of the retaining pin therethrough.

7. An applicator as claimed in claim 1 in which the stroke of the pushrod is limited by the stop face of the pusher abutting the crimping lever.

8. An applicator as claimed in claim 1 including a trigger for operating the pushrod and in which the trigger includes a visual indicator for indicating an intermediate trigger position.

\* \* \* \* \*